(12) United States Patent
Hu

(10) Patent No.: US 9,598,357 B1
(45) Date of Patent: *Mar. 21, 2017

(54) PROCESS FOR PRODUCING TAURINE FROM ALKALI TAURINATES

(71) Applicant: VITAWORKS IP, LLC, North Brunswick, NJ (US)

(72) Inventor: Songzhou Hu, Princeton, NJ (US)

(73) Assignee: VITAWORKS IP, LLC, North Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/998,888

(22) Filed: Feb. 29, 2016

(51) Int. Cl.
| | | |
|---|---|---|
| *C07C 303/22* | (2006.01) | |
| *C07C 303/44* | (2006.01) | |
| *B01J 27/08* | (2006.01) | |
| *B01J 27/10* | (2006.01) | |
| *B01J 27/053* | (2006.01) | |
| *B01J 27/055* | (2006.01) | |
| *B01J 27/02* | (2006.01) | |
| *B01J 27/25* | (2006.01) | |
| *B01J 27/18* | (2006.01) | |
| *B01J 27/232* | (2006.01) | |
| *B01J 31/04* | (2006.01) | |

(52) U.S. Cl.
CPC ............ *C07C 303/22* (2013.01); *B01J 27/02* (2013.01); *B01J 27/053* (2013.01); *B01J 27/055* (2013.01); *B01J 27/08* (2013.01); *B01J 27/10* (2013.01); *B01J 27/1806* (2013.01); *B01J 27/232* (2013.01); *B01J 27/25* (2013.01); *B01J 31/04* (2013.01); *C07C 303/44* (2013.01); *B01J 2231/005* (2013.01); *B01J 2531/002* (2013.01)

(58) Field of Classification Search
CPC ...... C07C 303/22; C07C 303/44; B01J 27/10; B01J 27/08; B01J 27/1806; B01J 27/053; B01J 27/02; B01J 27/25; B01J 27/065; B01J 27/232; B01J 31/04; B01J 2531/002; B01J 2231/005
See application file for complete search history.

(56) References Cited

U.S. PATENT DOCUMENTS

| | | | | |
|---|---|---|---|---|
| 4,861,844 | A * | 8/1989 | Lebrun | ................. C04B 35/571 525/474 |
| 5,362,891 | A * | 11/1994 | Bonaldi | ............... C07J 41/0061 552/554 |
| 8,609,890 | B1 | 12/2013 | Hu | |
| 9,061,976 | B1 * | 6/2015 | Hu | ........................ C07C 303/32 |
| 9,428,450 | B2 * | 8/2016 | Hu | ........................ C07C 303/02 |
| 9,428,451 | B2 * | 8/2016 | Hu | ........................ C07C 303/44 |
| 2014/0121405 | A1 | 5/2014 | Chen | |
| 2015/0299113 | A1 | 10/2015 | Hu | |
| 2015/0299114 | A1 | 10/2015 | Hu | |

* cited by examiner

*Primary Examiner* — Shailendra Kumar
(74) *Attorney, Agent, or Firm* — Graham Curtin, P.A.

(57) ABSTRACT

The present invention discloses a process and catalysts for producing taurine by catalytic ammonolysis of alkali ditaurinate, alkali tritaurinate, and their mixture. Useful catalysts are the ammonium and alkali salts of sulfate, bisulfate, sulfite, bisulfite, carbonate, bicarbonate, nitrate, phosphate, and organic carboxylic acids.

9 Claims, No Drawings

PROCESS FOR PRODUCING TAURINE FROM ALKALI TAURINATES

TECHNICAL FIELD

The present invention relates to a process for preparing taurine by catalytic ammonolysis of alkali ditaurinate, alkali tritaurinate, and their mixture to alkali taurinate.

DESCRIPTION OF THE INVENTION

Taurine can be referred to as 2-aminoethanesulfonic acid and is one of the amino sulfonic acids found in the tissues of many animals. Taurine is an extremely useful compound because it has such pharmacological effects as detoxification effect, fatigue-relieving effect and nourishing and tonifying effect. As a result, taurine finds wide applications as an essential ingredient for human and animal nutrition.

Taurine is currently produced in an amount of over 50,000 tons per year from ethylene oxide and monoethanolamine. At present time, most of the taurine is produced from ethylene oxide, following a three-step process: (1) the addition reaction of ethylene oxide with sodium bisulfite to yield sodium isethionate; (2) the ammonolysis of sodium isethionate to yield a mixture of sodium taurinate, sodium ditaurinate, and sodium tritaurinate; (3) the neutralization with an acid, i.e., hydrochloric acid and, preferably, sulfuric acid, to generate taurine and inorganic salts.

For the existing process of ethylene oxide, there are three detrimental disadvantage: i.e., the low production yield of 75-80%, the formation of large quantity of inorganic salt, and production of organic impurities that are difficult to dispose of.

U.S. Pat. No. 8,609,890 and U.S. Application No. 2014/0121405 disclose a cyclic process to eliminate the formation of sodium sulfate by substituting sulfuric acid with sulfur dioxide. In this process, sodium bisulfite, generated in the neutralization step, is used to react with ethylene oxide to yield sodium isethionate. However, the process could not be carried out indefinitely and the final yield is still no more than 80%, because of the accumulation of organic impurities, now identified as sodium ditaurinate and sodium tritaurinate.

According to U.S. Pat. No. 9,061,976, the production yield for the sulfur dioxide process is increased to nearly quantitative, when the byproducts, alkali ditaurinate and alkali tritaurinate, are converted to alkali taurinate.

U.S. Application No. 2015/0299113 and 2015/0299114 disclose a cyclic process for producing taurine from alkali isethionate in nearly quantitative yield. These two applications describe a fundamental reaction for the ammonolysis of the production byproducts, alkali ditaurinate and alkali tritaurinate, to alkali taurinate.

According to these prior arts, in order to convert the byproducts to alkali taurinate, alkali ditaurinate and alkali tritaurinate are first converted from their neutral forms to their basic forms, i.e., di-alkali ditaurinate and tri-alkali tritaurinate, by reacting with excess alkali hydroxide or alkali carbonate. After ammonolysis and removal of excess ammonia, additional acid is required to neutralize the base introduced into the reaction system. Therefore, additional inorganic salts, sodium sulfate for the sulfuric acid process and sodium sulfite for the sulfur dioxide process, are generated.

It is an object of the present invention to overcome the disadvantage of the ammonolysis of alkali ditaurinate and alkali tritaurinate to alkali taurinate in prior arts, and to provide advantages, which will become apparent from the following description.

It is another object of the present invention to disclose a process and effective catalysts for the catalytic ammonolysis of alkali ditaurinate and alkali tritaurinate to alkali taurinate in their available, neutral forms. More importantly, useful catalysts are found among neutral compounds that require no additional acid for processing after ammonolysis. Thereafter, no additional inorganic salts are generated for the ammonolysis step.

The present inventor has discovered that alkali ditaurinate, alkali tritaurinate, and their mixture can be converted to a mixture of mainly alkali taurinate through catalytic ammonolysis in the presence of catalysts without first reacting with a base, i.e., an alkali hydroxide or alkali carbonate, to form di-alkali ditaurinate and tri-alkali tritaurinate.

The process according to the present invention starts with mixing a solution of ditaurine, alkali ditaurinate, tritaurine, alkali tritaurinate, and their mixture with one or more catalysts, followed by an excess of ammonia. The ammonolysis is usually carried out at a temperature from 160° C. to 260° C. under the pressure from autogenous to 260 bars for 1 to 6 hours.

Useful catalysts are discovered among the neutral ammonium and alkali salts of sulfate, bisulfate, sulfite, bisulfite, carbonate, bicarbonate, nitrate, phosphate, chlorate, perchlorate, and organic carboxylic acids. Such salts are ammonium sulfate, lithium sulfate, sodium sulfate, potassium sulfate, ammonium bisulfate, sodium bisulfate, potassium bisulfate, ammonium sulfite, ammonium hydrogen sulfite, sodium sulfite, sodium metabisulfite, potassium sulfite, potassium bisulfite, lithium carbonate, lithium bicarbonate, sodium carbonate, sodium bicarbonate, potassium carbonate, and potassium bicarbonate. Useful organic acids are $C_1$-$C_{12}$ monocarboxylic acid, dibasic acids, aromatic acid, and hydroxy acids. The organic acids are, but not limited to, formic acid, acetic acid, propionic acid, butyric acid, glycolic acid, malic acid, tartaric acid, oxalic acid, succinic acid, adipic acid, citric acid, and benzoic acid.

Although the alkali salts of carbonate and bicarbonate are effective catalyst, their use is not preferred, because additional acid is needed to generate taurine from alkali taurinate after ammonolysis. But ammonium carbonate and ammonium bicarbonate can be used as catalysts since they can be recovered and separated from the ammonolysis solution by distilling with the recovery of excess ammonia.

Although the preferred catalysts are neutral ammonium and alkali salts, their use with a base, such as alkali hydroxide and alkali carbonate is also effective. However, no advantage will be gained in such combination, since additional amount of acid will be required for recovering taurine from the ammonolysis mixture.

The catalyst used in the ammonolysis reaction for alkali ditaurinate, alkali tritaurinate, and their mixture can be one component, but can also be a combination of two or more components. Catalysts exogenous to the reaction systems can be used, but catalysts inherently present in the production process are preferred. For the sulfuric acid process, alkali salts of sulfate are preferred, while alkali salts of sulfite are preferred in the sulfur dioxide process.

The amount of the catalyst used is not limited, but is usually from 0.01 to 10 in molar ratio of the catalyst to ditaurinate. The amount can be selected by those skilled in the art for the ammonolysis reaction to reach the equilibrium in desired time.

Table I and Table II in the Example 1 and Example 2 demonstrate the usefulness of the catalysts for the ammonolysis of ditaurine and tritaurine to taurine, respectively. It should be emphasized that no conversion to alkali taurinate is observed if no catalyst is added. It is interesting to note that the neutral alkali salts of halides, such as sodium chloride, potassium chloride, and sodium bromide, are not effective as catalysts at all, even in the presence of large amount. For useful and effective catalysts, taurine or sodium taurinate is obtained in a yield of about 70%, because the ammonolysis has reached the equilibrium under the preset experimental conditions.

Table III demonstrates the effect of increasing molar ratio of ammonia to ditaurine or sodium ditaurinate on the yield of taurine in the catalytic ammonolysis reaction. Complete conversion to taurine can be attained by increasing the molar ratio of ammonia to taurine to 40 fold. However, such a large of excess of ammonia in the production is impractical, because the recovery of excess amount of ammonia and removal of water from the reaction mixture requires excessive amount of energy.

Although the yield of taurine is obtained in a yield of about 70% for each ammonolysis reaction under industrially suitable conditions, the final yield of taurine reaches nearly quantitative after the mother liquor containing the alkali ditaurinate and alkali tritaurinate is subjected to the ammonolysis reaction in successive cycles.

Optionally, the mother liquor can be combined with a new batch of alkali taurinate and alkali tritaurinate.

The process according to the present invention can be carried out discontinuously, semi-continuously, and continuously.

EXAMPLES

The following examples will illustrate the practice of this invention but are not intended to limit its scope.

Example 1

This set of examples relates to the ammonolysis of ditaurine and sodium ditaurinate in the presence of catalysts. The results are shown in the Table I.

All examples are for 0.05 mole of ditaurine or sodium ditaurinate, dissolved in 50 mL of 20% ammonia in a molar ratio of 1:7 for taurine/ammonia. The ammonolysis reaction is carried out in an 100 mL autoclave at 210° C. under autogenous pressure for 2 hours. The content of taurine is assayed by HPLC analysis.

TABLE I

Ammonolysis of Ditaurine and Sodium Ditaurinate to Taurinate

| Ex | Catalyst | Amount Molar ratio | Ditaurine to Taurine (yield %) | Sodium Ditaurinate to Taurine (yield %) |
|---|---|---|---|---|
| 1 | None | | 0 | 3 |
| 2 | Sodium Chloride | 1.2 | 0 | 4 |
| 3 | Potassium Chloride | 1.2 | 0 | 3 |
| 4 | Lithium Chloride | 1.2 | 0 | 2 |
| 5 | Sodium Bromide | 1.2 | 0 | 3 |
| 6 | Ammonium Sulfate | 0.5 | 68 | 72 |
| 7 | Sodium Sulfate | 0.1 | 74 | 75 |
| 8 | Sodium Sulfate | 0.5 | 73 | 74 |
| 9 | Sodium Sulfate | 1.0 | 75 | 74 |
| 10 | Potassium Sulfate | 0.1 | 73 | 75 |
| 11 | Sodium Sulfite | 0.1 | 74 | 75 |
| 12 | Sodium Nitrate | 0.1 | 74 | 74 |
| 13 | Sodium Phosphate | 0.1 | 75 | 74 |
| 14 | Ammonium Carbonate | 0.1 | 69 | 71 |
| 15 | Sodium Thiosulfate | 0.1 | 65 | 69 |
| 16 | Sodium Benzoate | 0.1 | 69 | 72 |
| 17 | Ammonium Acetate | 0.1 | 68 | 69 |
| 18 | Sodium Acetate | 0.1 | 71 | 72 |
| 19 | Potassium Acetate | 0.1 | 70 | 71 |
| 20 | Sodium Oxalate | 0.1 | 72 | 73 |
| 21 | Sodium Malate | 0.1 | 72 | 74 |
| 22 | Sodium Succinate | 0.1 | 73 | 74 |
| 23 | Sodium Tartrate | 0.1 | 73 | 73 |
| 24 | Potassium Tartrate | 0.1 | 72 | 74 |
| 25 | Sodium Citrate | 0.1 | 73 | 75 |
| 26 | Potassium Citrate | 0.1 | 74 | 75 |

Example 2

This set of examples relates to the ammonolysis of tritaurine and sodium tritaurinate in the presence of catalysts. The results are shown in the Table II.

All examples are for 0.03 mole of tritaurine or sodium tritaurinate, dissolved in 55 mL of 20% ammonia in a molar ratio of 1:7 for taurine/ammonia. The ammonolysis reaction is carried out in an 100 mL autoclave at 210° C. under autogenous pressure for 2 hours. The content of taurine is assayed by HPLC analysis. The starting pH of sodium tritaurinate is 6.0.

TABLE II

Ammonolysis of Tritaurine and Sodium Tritaurinate to Taurinate

| Ex | Catalyst | Amount Molar ratio | Tritaurine to Taurine (%) | Sodium Tritaurinate to Taurine (%) |
|---|---|---|---|---|
| 27 | None | | 0 | 3 |
| 28 | Sodium Chloride | 1.2 | 0 | 2 |
| 29 | Ammonium Sulfate | 0.5 | 66 | 71 |
| 30 | Sodium Sulfate | 0.1 | 74 | 75 |
| 31 | Sodium Sulfate | 0.5 | 75 | 74 |
| 32 | Sodium Sulfate | 1.0 | 75 | 75 |
| 33 | Potassium Sulfate | 0.1 | 73 | 74 |
| 34 | Sodium Sulfite | 0.1 | 72 | 73 |
| 35 | Ammonium Carbonate | 0.1 | 67 | 70 |
| 36 | Ammonium Acetate | 0.1 | 68 | 71 |
| 37 | Sodium Acetate | 0.1 | 72 | 71 |
| 38 | Potassium Acetate | 0.1 | 72 | 73 |
| 39 | Sodium Oxalate | 0.1 | 71 | 74 |
| 40 | Sodium Malate | 0.1 | 73 | 74 |
| 41 | Sodium Succinate | 0.1 | 72 | 74 |
| 42 | Sodium Tartrate | 0.1 | 72 | 73 |
| 43 | Potassium Tartrate | 0.1 | 71 | 74 |
| 44 | Sodium Citrate | 0.1 | 74 | 74 |

Example 3

This set of examples shows the effect of increasing molar ratio of ammonia to ditaurine on the yield of taurine. The experiment starts with 0.05 mole ditaurine or sodium ditaurinate (corresponding to 0.1 mole of taurine) in 42.5 g of 20% ammonia solution and 5 g of sodium sulfate. The ammonolysis reaction is carried out at 210° C. under autogenous pressure for 2 hours. The amount of ammonia is increased by 42.5 g of 20% ammonia solution in each successive tests. The content of taurine is assayed by HPLC analysis. The results are shown in Table III.

TABLE III

Effect of Ammonia on the Catalytic Ammonolysis of Ditaurinate and Sodium Ditaurinate to Ditaurine

| Ex | Molar Ratio Ammona/taurine | Ditaurine to Taurine (%) | Sodium Ditaurinate to Taurine (%) |
|---|---|---|---|
| 45 | 5 | 64 | 65 |
| 46 | 10 | 76 | 78 |
| 47 | 15 | 81 | 83 |
| 48 | 20 | 91 | 93 |
| 49 | 25 | 94 | 95 |
| 50 | 30 | 98 | 98 |
| 51 | 35 | 99 | 99 |
| 52 | 40 | 100 | 100 |

Example 4

This example demonstrates the conversion of sodium ditaurinate and sodium tritaurinate in the recrystallization mother liquor to sodium taurinate in the sulfuric acid process.

To 200 mL of the mother liquor from $2^{nd}$ cooling crystallization stage from U.S. Application No. 2015/0299113, composed of sodium ditaurinate (25% by wt), sodium tritaurinate (3% by wt), taurine (5% by wt), and sodium sulfate (6% by wt), is added 500 mL of 25% aqueous ammonia. The solution is heated in a 2 L autoclave at 210° C. for 2 hours to carry out the ammonolysis reaction.

HPLC and LC-MS analysis shows that the reaction solution is comprised of the following taurinates: sodium taurinate (75%), sodium ditaurinate (22%), and sodium tritaurinate (3%) on the molar basis.

After the ammonolysis, excess ammonia in the reaction solution is removed by distilling to 103° C. Then sulfuric acid is added to adjust the pH to 7.5. After cooling to 30-35° C. under stirring, a mass of crystalline taurine is formed. Filtration, washing with deionized water, and drying yield 41.6 g of taurine with a purity of 98%.

It will be understood that the foregoing examples, explanation, and tables are for illustrative purposes only and that in view of the instant disclosure various modifications of the present invention will be self-evident to those skilled in the art and are to be included within the spirit and purview of this application and the scope of the appended claims.

What is claimed is:

1. A process for producing taurine from alkali ditaurinate, alkali tritaurinate, or their mixture, comprising,
   (a) adding one or a combination of two or more catalysts and an excess amount of ammonia to a solution of alkali ditaurinate, alkali tritaurinate, or their mixture;
   (b) subjecting the solution of (a) to ammonolysis reaction;
   (c) removing excess ammonia and neutralizing with an acid to obtain a crystalline suspension of taurine; and
   (d) recovering taurine by solid-liquid separation.

2. The process according to claim 1, wherein the catalysts are selected from the group consisting of the ammonium and alkali salts of hydroxide, sulfate, bisulfate, carbonate, bicarbonate, sulfite, bisulfate, phosphate, nitrate, and organic carboxylic acids.

3. The process according to claim 1, wherein the amount of catalyst in molar ratio relative to ditaurine, tritaurine, or their mixture is from 0.01 to 10.

4. The process according to claim 2, wherein the alkali are selected from the group consisting of lithium, sodium, potassium, and cesium.

5. The process according to claim 2, wherein the organic carboxylic acids are selected from the group consisting of $C_1$-$C_{12}$ monocarboxylic acid, dibasic carboxylic acid, aromatic acid, and hydroxy carboxylic acids.

6. The process according to claim 5, wherein the organic carboxylic acids are selected from the group consisting of formic acid, acetic acid, propionic acid, butyric acid, glycolic acid, malic acid, tartaric acid, oxalic acid, succinic acid, adipic acid, citric acid, and benzoic acid.

7. The process according to claim 1, wherein the acid is selected from the group consisting of hydrochloric acid, hydrobromic acid, sulfuric acid, nitric acid, and organic carboxylic acids.

8. The process according to claim 1, wherein the ammonolysis reaction is carried out at a temperature from 160° C. to 260° C. under the pressure from autogenous to 260 bars.

9. The process of claim 1 further comprising after step (d):
   (e) returning the mother liquor to (a) for further ammonolysis.

* * * * *